United States Patent [19]

Bailey et al.

[11] Patent Number: 4,827,053
[45] Date of Patent: May 2, 1989

[54] PERFLUORINATED DI-ISOPROPYLMETHYL DECALIN

[75] Inventors: Webb I. Bailey, Fogelsville; Frank K. Schweighardt, Allentown; Varin Ayala, Catasauqua, all of Pa.

[73] Assignee: Air Products and Chemicals, Inc., Allentown, Pa.

[21] Appl. No.: 227,966

[22] Filed: Aug. 3, 1988

[51] Int. Cl.$^4$ .................. C07C 19/08; C07C 17/06
[52] U.S. Cl. .................. 570/130; 228/40; 514/832
[58] Field of Search .................. 570/130

[56] References Cited

U.S. PATENT DOCUMENTS

| | | | |
|---|---|---|---|
| 30,399 | 9/1880 | Ammann et al. | 228/180 |
| 2,459,782 | 1/1949 | McBee et al. | 570/130 |
| 2,487,820 | 11/1949 | McBee et al. | 260/648 |
| 2,631,170 | 4/1953 | Fowler | 260/648 |
| 3,775,489 | 11/1973 | Margrave et al. | 260/648 |
| 3,786,324 | 1/1974 | Kotschy | 317/258 |
| 4,106,557 | 8/1978 | Sonobe et al. | 165/105 |
| 4,143,079 | 3/1979 | Moore | 260/648 |
| 4,396,785 | 8/1983 | Kobayashi et al. | 570/129 |
| 4,453,028 | 6/1984 | Lagow | 570/130 |
| 4,549,686 | 10/1986 | Burgeut et al. | 228/242 |
| 4,739,112 | 4/1988 | Savv | 570/130 |

FOREIGN PATENT DOCUMENTS

| | | |
|---|---|---|
| 0194009 | 10/1986 | European Pat. Off. . |
| 785641 | 10/1957 | United Kingdom . |
| 1281822 | 7/1972 | United Kingdom . |
| 2110204 | 6/1983 | United Kingdom . |
| 2194231 | 3/1988 | United Kingdom . |

OTHER PUBLICATIONS

*Organic Fluorides Part V. Fluorination of Hydrocarbons with Cobalt Trifluoride*, R. N. Haszeldine & F. Smith, Journal of Chemistry Society (1950), pp. 3617–3623.

"Infra-red Spectra of Fluorinated Hydrocarbons", L. J. Bellamy, *Nature*, No. 4405, Vo. 173, Apr. 3, 1954, pp. 633–634.

"Ternary Systems of Sulfur and Sulfur Compounds", A. W. Francis, *Journal of Chemical and Engineering Data*, vol 11(4) 1966, pp. 557–562.

*Primary Examiner*—J. E. Evans
*Attorney, Agent, or Firm*—Geoffrey L. Chase; James C. Simmons; William F. Marsh

[57] ABSTRACT

Novel compositions include compounds of the formula:

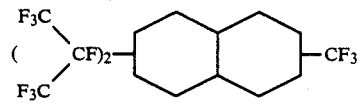

wherein the carbon rings are fully fluorinated.

4 Claims, No Drawings

PERFLUORINATED DI-ISOPROPYLMETHYL DECALIN

TECHNICAL FIELD

The present invention is related to the field of perfluorinated, alkyl-substituted, condensed ring compounds. More specifically, the present invention is directed to di-propyl, methyl derivatives of decahydronaphthalene (decalin) prepared from naphthalene, which former compound is then fully fluorinated.

BACKGROUND OF THE PRIOR ART

Fluorinated carbon compounds are finding increasing utility in modern industry, such as the electronics fabrication industry, and researchers have found heightened interest in fluorinated compounds for various biological and medical applications, such as synthetic blood and diagnostic fluids.

Perfluorinated multiple condensed ring compounds have been known for a significant period of time, such as perfluorophenanthrene as disclosed in U.S. Pat. No. 2,487,820. That patent makes a broad, general and unsupported disclosure that:

"Fused-ring aromatic hydrocarbons such as anthracene, naphthalene, phenanthrene and their substitution derivatives, can be fluorinated readily with the addition of fluorine atoms at the points of unsaturation and, if desired, with the replacement of hydrogen in the molecule, and the production of saturated fluorine-containing compounds."

Partially fluorinated compounds are exemplified by the 1-methyl-(3,3,3-trifluoropropyl)naphthalene compounds disclosed in U.S. Pat. No. 4,396,785. These compounds are only marginally fluorinated and the condensed carbon rings retain their unsaturated aromatic character.

The tertiary butyl derivatives of a single carbon ring, cyclohexene, is disclosed in U.S. Pat. No. 4,453,028.

Perfluoro-2-methyldecahydronaphthalene has been reported to have been synthesized from 2-methyl naphthalene using cobalt trifluoride fluorination technology as set forth in an article titled *Organic Fluorides. Part V. Fluorination of Hydrocarbons With Cobalt Trifluoride*, by R. N. Haszeldine and F. Smith appearing in Journal of Chemistry Society (1950) pages 3617 to 3623.

The cobalt trifluoride fluorination of 1-methyl decalin to produce perfluoro-1-methyl decalin has also been set forth in British Pat. No. 1,281,822. Fluorination of substituted naphthalenes is generally disclosed.

The basic technique for cobalt trifluoride fluorination is set forth in U.S. Pat. No. 2,631,170.

U.S. Pat. Nos. 3,775,489 is directed to the fluorination of various aromatic carbon compounds of the naphthalene and anthracene class.

U.S. Pat. No. 3,786,324 discloses a utility for perfluorinated hydrocarbons comprising dielectric fluids for capacitors. The compound 1-trifluoromethylperfluorodecalin is mentioned as a potential dielectric fluid.

U.S. Pat. No. 4,106,557 describes a refrigeration apparatus utilizing various halogenated carbon refrigerants, including cyclic fluorinated carbon ethers.

U.S. Pat. No. 4,143,079 discloses a perfluorinated 1-methyl-4-isopropyl cyclohexane. This material is recited to have utility as an artificial blood component.

U.S Pat. No. Re. 30,399 discloses a technique for soldering electronic components in a mass production mode in the heated vapor of a boiling fluid wherein the vapor condenses on cold solder to be reflowed and the solder is melted by the heat of vaporization evolved during the condensation of the adhering fluid vapor. This form of soldering is known as vapor phase soldering, condensation soldering and various reflow soldering nomenclatures. The criteria delineated for a heat transfer liquid for such soldering includes: a boiling point above the melting point of the solder wherein the boiling point is preferably sharply defined and dependent upon a single component rather than multicomponent materials, electrically non-conducting characteristics, vapors which are non-oxidizing, chemically stable and inert, non-toxic, non-inflammable and relatively denser than air, relatively high latent heat of vaporization, and degreasing properties. Fluorinated polyoxypropylene is a disclosed fluorocarbon suitable for heat transfer liquid choice.

L. J. Bellamy, in an article in *Nature*, No. 4405, Vol. 173, Apr. 3, 1954, pp. 633–634, discusses the infra-red spectra of several dimethyl decalin perfluorinated compounds.

A. W. Francis, in an article in *Journal of Chemical and Engineering Data*, Vol. 11 (4) 1966, pp. 557–562 mentions perfluoro-1-methylnaphthalene and perfluoro-1-nonylnaphthalene.

U.S. Pat. No. 4,549,686 describes vapor phase soldering using perfluorotetradecahydrophenanthrene (perfluorophenanthrene).

British Pat. No. 785,641 discloses the fluorination of various carbon compounds with hydrogen fluoride wherein such compounds include benzene, toluene, anthracene and diamylnaphthalene. Retene, which is 1-methyl-7-isopropyl phenanthrene, is also capable of the recited fluorination treatment.

U.K. Patent Application No. 2110204A discloses various perfluoroalkyl-cyclohexane mixtures useful for vapor phase soldering in the boiling range of 180° to 300° C. These materials are produced by the fluorination of narrow cut linear alkylbenzene compounds with cobalt trifluoride.

European Patent Application No. 0 194 009 disloses fluorochemical compositions comprising compounds in the form of perfluoropolycycloalkane ring assemblies having (a) at least two perfluorinated cyclohexane rings, (b) at least two perfluorinated fused ring systems, or (c) a combination of at least one perfluorinated fused ring system with at least one perfluorinated cyclohexane ring, each perfluorinated ring or ring system being directly joined to another perfluorinated ring or fused ring system by a single bond. The rings may have certain substituent groups.

U.K. Patent Application GB No. 2,194,231A discloses generally $C_{17}$ fluorinated compounds useful as vapor phase soldering fluids. The application expressly teaches away from branched alkyl derivatives of polycyclics at page 1, line 65 through page 2, line 2.

The prior art fluorination compounds have failed to provide a stable, inert perfluoro compound having a desirable sharp boiling point in the approximate range of 250°–265° C. which is most desirable for presently existing vapor phase soldering utilities. In addition, the prior art compounds suffer from various levels of susceptibility to heat degradation to hydrogen fluoride and perfluoroisobutylene, as well as having undesirable fluorine utilizations due to significant levels of aliphatic character. The present invention overcomes these shortcomings.

BRIEF SUMMARY OF THE INVENTION

The present invention is a perfluorinated compound of the formula:

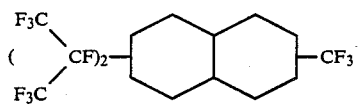

wherein the carbon rings are fully fluorinated.

One of the preferred species of the compounds of the present invention is the 4,7-perfluorodiisopropyl-2-perfluoro methyl substituted decalin compound. Another preferred compound is the perfluorodiisopropyl methyl substituted decalin wherein the propyl substitution is in the 4 and 8 positions.

The present invention is also directed to a method for utilizing such compounds wherein it comprises a method of soldering a component to be soldered by immersing a component in the vapor bath to melt the solder, and the component is then withdrawn from the vapor bath, the improvement comprising that the vapor bath is composed substantially of compounds having the formula:

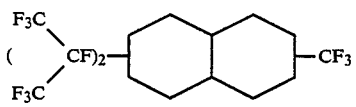

wherein the carbon rings are fully fluorinated. The vapor bath can comprise mixtures of the recited compounds with other compounds such as perfluorophenanthrene.

DETAILED DESCRIPTION OF THE INVENTION

The various perfluorinated isopropyl, methyl derivatives of decalin, which constitute the subject matter of the present invention, are valuable as inert constant boiling fluids required by the electronic fabrication industry for the manufacture and testing of various electronic components. Fluids boiling in the temperature range of 250°–265° C. are of interest to the electronics industry for these applications. Currently, various suppliers of fluorinated fluids provide a series of compounds that meet the 150°–265° C. temperature range which are based on, for example, perfluorinated tertiary amines. There is some question on the stability of these materials at elevated temperatures. One concern arises from incomplete fluorination, which results in residual hydrogen. These partially fluorinated compounds have been shown to undergo decomposition at elevated temperatures resulting in the formation of HF and perfluoroisobutylene.

Another class of compounds that are currently supplied to meet the needs for a 150°–265° C. boiling fluid are based on perfluoropolyethers. These polyethers are prepared by the oxidative polymerization of tetrafluoroethylene. To obtain the various boiling ranges, the polyethers are distilled into different fractions. The final product does not constitute a single compound, but rather a mixture of molecular weight ranges. This results in a product, that with time will increase in boiling temperature as the lower molecular weight fractions are removed by differential boil-off.

The compositions of the present invention constitute essentially single compounds having sharply defined boiling points which do not fractionate off into various components through exposure to cycling from cooldown to high temperature utilization, such utilization as is characteristic of vapor phase soldering fluid utility. For the sake of clarity the numbering of the carbons on the decalin ring (fully saturated naphthalene derivtive) are set forth below.

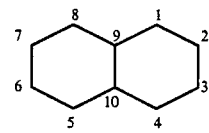

The perfluorodiisopropylmethyldecalin compound of the present invention, which is preferably substituted with isopropyl at the number 4 and 7 or 8 position of the decalin ring and at the 2 position of the decalin ring with methyl, has an empirical formula of $C_{17}F_{32}$ and a molecular weight of 812. The material is a liquid at room temperature with a boiling point of approximately 250°–265° C. The general structure of the compound of the present invention has been confirmed by $^{19}F$ NMR (nuclear magnetic resonance spectroscopy) and GC/MS (gas chromatography/mass spectroscopy). Typically, the feedstock to produce such a perfluorinated compound is the hydrocarbon diisopropylmethylnaphthalene, which can be prepared by the alkylation of naphthalene by known techniques. The new composition of the present invention is substantially a perfluorinated analog of the above hydrocarbon starting material wherein all aromatic character and hydrogen are removed as a result of the reaction process. All isomers and conformers of diisopropylmethylnaphthalene are represented by the perfluorinated compound of the present invention.

All of these species of the compounds of the present invention have utility for oxygen transport media for in vivo and in vitro use as pure substances or mixtures or emulsions, as well as use as hydraulic fluids, lubricants, heat exchange or cooling fluids and other such applications where chemical inertness and boiling point are the desired physical and chemical properties, most particularly vapor phase soldering. Various of the compounds have been tested as vapor phase soldering fluids. The fluids were heated at reflux for an extended period of time and showed no evidence of decomposition, wherein a printed circuit board which contained a solder silk screen and a surface mounted device was immersed into the reflux vapor area and the solder reflow occurred within 30 seconds. This demonstrated successful and acceptable vapor phase soldering utility.

At this time, the preparation and identification of the compounds of the present invention will be set forth in the following examples and tables.

EXAMPLE 1

50.00 g of di-isopropylmethyl naphthalene were charged to a sample cylinder and connected to an enclosed hotplate operating at 300° C. The diisopropylmethyl naphthalene was fed into the hotplate by a metering pump at a rate of 12.5 g/hr into a 15.5 sccm nitrogen stream. The organic/nitrogen stream was carried into a cobalt trifluoride reactor 10 cm in diameter and 60 cm long containing approximately 3000 g cobalt trifluoride. The reactor was heated to 280° C. The diisopropylmethyl naphthalene feed was subsequently converted to a perfluorochemical in the reactor and was collected in a trap held at 25° C. 74.2 g of a light yellow liquid were collected representing a 41% yield. Additional material was produced under similar conditions.

EXAMPLE 2

205.3 g of the combined cobalt trifluoride products of Example 1 were charged to a 1.0 liter stainless steel sample cylinder for a direct fluorination clean-up step. A fluorine/nitrogen gas mixture increasing to 100% fluorine with time was sparged into the liquid at 25° C. and 150° C.

EXAMPLE 3

175.1 g of the directly fluorinated product from Example 2 above was distilled. A fraction boiling at 255° C. was collected which represented 30.6% (by weight) of the total sample. A fraction boiling at 219° C., which represented 40.8% of the total sample was also collected. The perfluorochemicals were identified as perfluoro diisopropylmethyl decalin and perfluoro isopropylmethyl decaline, respectively. Analytical information is shown in Table 1.

TABLE 1

| PERFLUORO DI-ISOPROPYLMETHYL DECALIN |
|---|
| $^a$NMR - $^{19}$F |

| $CF_3$ | $CF_2$ | $CF$ |
|---|---|---|
| −65 to −85$^b$ multiplet | −100 to −130$^b$ multiplet | −170 to −190$^b$ multiplet |

| $^c$MASS SPECTRUM (m/e) | |
|---|---|
| calculated | 812 ($C_{17}F_{32}$) |
| observed | 812 ($C_{17}F_{32}$) |

$^a$in $CCl_3F/D_2O$ (capillary)
$^b$ppm from $CCl_3F$
$^c$electron ionization and/or chemical ionization with $CH_4$

EXAMPLE 4

A glass vapor phase soldering apparatus consisting of a 100 ml flask connected to a condenser can be used to demonstrate vapor phase soldering with perfluoro diisopropylmethyl decalin. A solder paste consisting of 96.5% tin and 3.5% silver is used to coat a printed circuit board and a surface mount device is positioned on the solder paste. The entire assemble can be immersed into perfluoro diisopropylmethyl decalin vapors which had been heated to reflux temperature and solder reflow would be observed to occur in approximately 30 seconds. Upon removal of the circuit assembly, no fluorochemical residue would be observed, but rather clean substantial reflow of the solder. The surface mount device and the printed circuit board would be firmly affixed together by the operation of the solder.

These compounds of the present invention have particularly desirable utility in a method of soldering a component to be soldered by immersing a component in the vapor bath to melt the solder, and the component is then withdrawn from the vapor bath, the improvement comprising that the vapor bath is composed substantially of compounds having the formula:

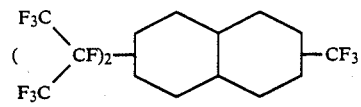

wherein the carbon rings are fully fluorinated. The compounds can be mixed with one another or other compounds such as perfluorophenanthrene. Vapor phase soldering is described in U.S. Pat. No. Re. 30,399 and U.S. Pat. No. 4,549,686, both of which are incorporated herein by reference.

The compounds of the present invention succeed in overcoming the drawbacks of various of the compounds of the prior art, particularly for utility in vapor phase soldering fluid use. The compounds of the present invention exhibit all of the desired attributes of a vapor phase soldering fluid as identified in U.S. Pat. No. Re. 30,399 described above. Included in these attributes which the compounds in the present invention exhibit are: low toxicity, chemical inertness, lack of flammability, appropriate dielectric characteristics, degreasing properties, sharply defined boiling point, a vapor denser than air and relatively high latent heat of vaporization. Specifically, these compounds have low potential for evolution of HF and perfluoroisobutylene when subjected to long term cyclic heating and cooling typical of vapor phase soldering use.

The present invention has been set forth with regard to various specific examples and embodiments of the invention. However, the scope of the invention should be ascertained from the claims which follow.

We claim:

1. The perfluorinated compounds of the formula:

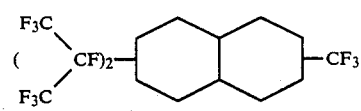

wherein the carbon rings are fully fluorinated.

2. The perfluorinated compounds of claim 1 having the formula:

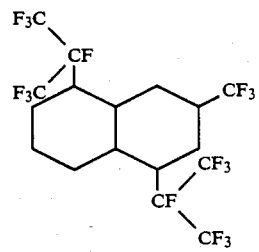

3. The perfluorinated compounds of claim 1 having the formula:

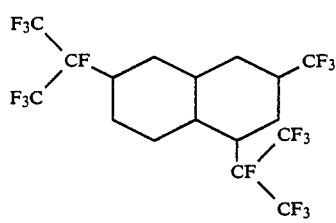
4. The perfluorinated compounds of claim 1 having the formula:
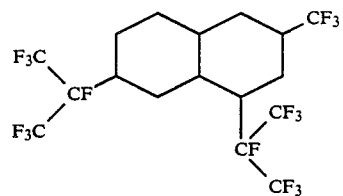
* * * * *